United States Patent
Yuasa

(10) Patent No.: US 8,992,017 B2
(45) Date of Patent: Mar. 31, 2015

(54) OPHTHALMOLOGIC APPARATUS

(71) Applicant: Canon Kabushiki Kaisha, Tokyo (JP)

(72) Inventor: Takashi Yuasa, Sagamihara (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 13/904,780

(22) Filed: May 29, 2013

(65) Prior Publication Data

US 2013/0321771 A1  Dec. 5, 2013

(30) Foreign Application Priority Data

Jun. 1, 2012 (JP) ................................ 2012-126191

(51) Int. Cl.
A61B 3/14 (2006.01)
A61B 3/10 (2006.01)
A61B 3/15 (2006.01)

(52) U.S. Cl.
CPC ................ *A61B 3/1025* (2013.01); *A61B 3/14* (2013.01); *A61B 3/152* (2013.01)
USPC ........................... 351/208; 351/221; 351/206

(58) Field of Classification Search
USPC ............................................... 351/200–246
See application file for complete search history.

(56) References Cited

U.S. PATENT DOCUMENTS

| | | | |
|---|---|---|---|
| 6,337,993 B1 | 1/2002 | Kishida et al. | |
| 6,655,805 B2 | 12/2003 | Fujieda | |
| 7,527,379 B2 | 5/2009 | Yamaguchi et al. | |
| 7,635,186 B2 | 12/2009 | Kobayashi et al. | |
| 7,736,001 B2 | 6/2010 | Tanaka et al. | |
| 8,469,514 B2 | 6/2013 | Utsunomiya | |
| 8,506,081 B2 | 8/2013 | Matsumoto | |
| 8,596,785 B2 | 12/2013 | Imamura et al. | |
| 8,646,915 B2 | 2/2014 | Nozato | |
| 8,708,489 B2 | 4/2014 | Utagawa | |
| 2001/0056239 A1 | 12/2001 | Ono | |
| 2007/0216866 A1 | 9/2007 | Kobayashi et al. | |
| 2012/0019780 A1 | 1/2012 | Nozato | |
| 2012/0033180 A1 | 2/2012 | Pieri et al. | |
| 2013/0321765 A1 | 12/2013 | Yuasa | |
| 2013/0321766 A1* | 12/2013 | Morohashi | 351/206 |
| 2013/0321767 A1 | 12/2013 | Hirose | |
| 2013/0321768 A1 | 12/2013 | Utagawa | |

(Continued)

FOREIGN PATENT DOCUMENTS

JP  2002-200043 A  7/2002
JP  2003-126042 A  5/2003

(Continued)

*Primary Examiner* — Mohammed Hasan
(74) *Attorney, Agent, or Firm* — Canon U.S.A., Inc. IP Division

(57) ABSTRACT

An ophthalmologic apparatus includes a first light source configured to emit a first measuring beam, a second light source configured to emit a second measuring beam having a center wavelength longer than that of the first measuring beam, a third light source configured to emit a third measuring beam having a center wavelength shorter than that of the first measuring beam, a first acquisition unit configured to obtain a first image of the subject's eye by using the return beam of the second measuring beam from the subject's eye, aberration of which has been corrected by a correction unit, and a second acquisition unit configured to obtain an anterior eye portion image of the subject's eye to be used for alignment, by using a return beam of the third measuring beam from the subject's eye.

20 Claims, 8 Drawing Sheets

(56) References Cited

U.S. PATENT DOCUMENTS

2013/0321769 A1 12/2013 Kusumoto
2013/0321771 A1 12/2013 Yuasa

FOREIGN PATENT DOCUMENTS

| JP | 2004-033275 A | 2/2004 |
| JP | 2010-259543 A | 11/2010 |

* cited by examiner

OPHTHALMOLOGIC APPARATUS

BACKGROUND OF THE INVENTION

1. Field of the Invention

The present invention relates to an ophthalmologic apparatus.

2. Description of the Related Art

A scanning laser ophthalmoscope (SLO), which is an ophthalmologic apparatus using a principle of a confocal laser microscope, performs raster scanning for, for example, a fundus of a subject's eye with a laser that is a measuring beam, and acquires a planar image from intensity of its return beam from the subject's eye with high resolution at a high speed. Hereinafter, an apparatus for capturing such a planar image may be referred to as a SLO apparatus.

There is known a technology for measuring aberration of the subject's eye by a wavefront sensor in real time, and correcting the aberration of the subject's eye by a wavefront correction device. Japanese Patent Application Laid-Open No. 2010-259543 discusses an adaptive optics SLO (hereinafter, may be referred to as AOSLO apparatus) having an adaptive optical system for correcting the aberration by the wavefront correction device. By this technology, a planar image of high lateral resolution (hereinafter, may be referred to as AOSLO image) can be obtained.

The AOSLO apparatus uses a light source for obtaining an anterior eye portion image, a light source for obtaining a planar image of high lateral resolution, a light source for measuring aberration, a light used for obtaining a planar image of a wide angle of view when the planar image of high lateral resolution is obtained, and a light source for visual fixation.

However, in Japanese Patent Application Laid-Open No. 2010-259543, there is no mention of a relationship between a wavelength of the light source for obtaining the anterior eye portion image and the wavelengths of the other light sources.

SUMMARY OF THE INVENTION

The present invention is directed to obtaining of a highly accurate AOSLO image by using a light source wavelength relationship suited to an AOSLO apparatus. Not limited to this, the present invention is also directed to working-effects obtained by exemplary embodiments of the present invention described below which have not been achieved by the conventional art.

According to an aspect of the present invention, an ophthalmologic apparatus includes a first light source configured to emit a first measuring beam, a second light source configured to emit a second measuring beam having a center wavelength longer than that of the first measuring beam, a third light source configured to emit a third measuring beam having a center wavelength shorter than that of the first measuring beam, an aberration measurement unit configured to measure aberration caused by a subject's eye with use of a return beam of the first measuring beam from the subject's eye, a correction unit configured to correct aberration of a return beam of the second measuring beam from the subject's eye caused by the subject's eye based on the aberration measured by the aberration measurement unit, a first acquisition unit configured to obtain a first image of the subject's eye by using the return beam of the second measuring beam from the subject's eye, the aberration of which has been corrected by the correction unit, and a second acquisition unit configured to obtain an anterior eye portion image of the subject's eye to be used for alignment, by using a return beam of the third measuring beam from the subject's eye.

According to another aspect of the present invention, an ophthalmologic apparatus includes a plurality of light sources configured to emit measuring beams of different center wavelengths. An interval between the center wavelengths adjacent to each other is a value based on respective half-value full widths of the plurality of adjacent measuring beams.

According to the present invention, a highly accurate AOSLO image can be obtained by using a light source wavelength relationship suited to the AOSLO apparatus.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

The present invention is not limited to the exemplary embodiments described below. Various changes and modifications can be made within the scope of the present invention.

In the present exemplary embodiment, as an ophthalmologic apparatus, an AOSLO apparatus according to the the present invention will be described. The AOSLO apparatus, which includes an adaptive optical system, captures a high lateral resolution planar image of a fundus of a subject's eye.

For the purpose of assisting obtaining of the AOSLO image, the AOSLO apparatus includes a WFSLO unit for capturing a wide field angle planar image (WFSLO image). The AOSLO apparatus further includes an anterior eye portion observation unit for grasping an incident position of a measuring beam, and a fixation lamp unit for guiding a line of sight to adjust an imaging place.

In AOSLO apparatus according to the present embodiment, optical aberration caused by the subject's eye is corrected by using a spatial light modulator to obtain a planar image. Thus, a good planar image can be obtained by reducing an influence of a diopter scale or the optical aberration of the subject's eye.

In the embodiment, the AOSLO device includes the adaptive optical system to capture the high lateral resolution planar image. However, the adaptive optical system is unnecessary as long as the configuration can realize high resolution.

<Overall Configuration of Apparatus>

Figure 1A:
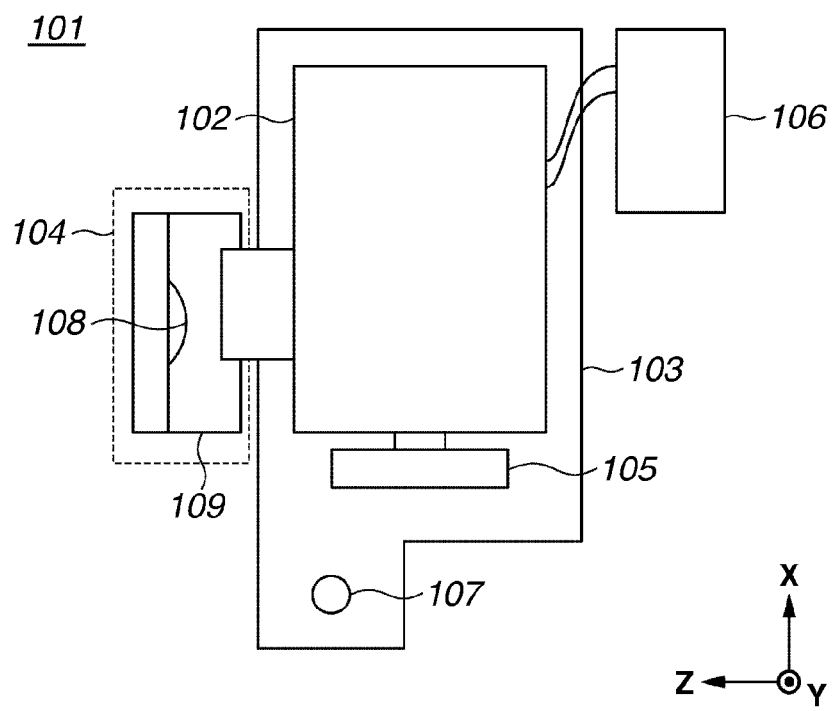
FIGS. 1A and 1B illustrate an example of an entire configuration of an AOSLO apparatus according to an exemplary embodiment of the present invention.
Figure 1B:
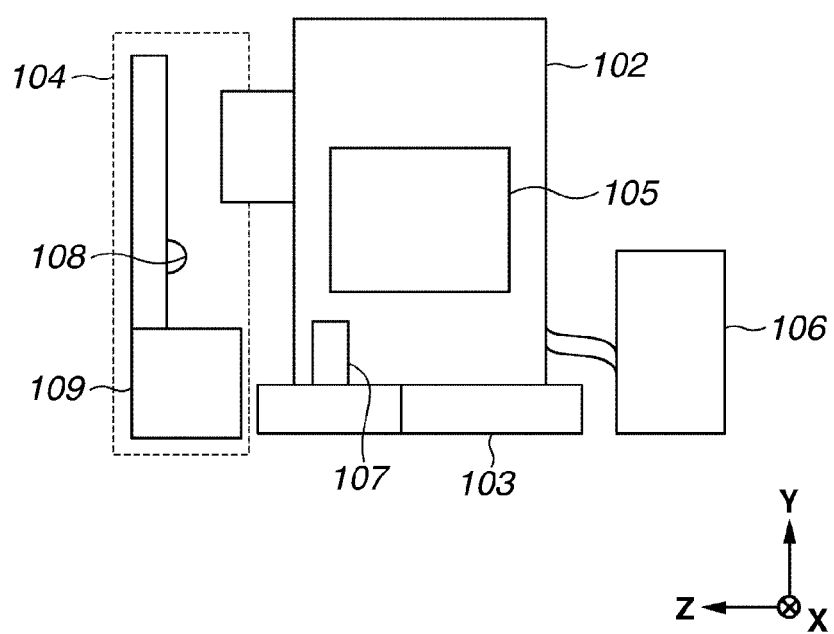

Referring to FIGS. 1A and 1B, a schematic configuration of the AOSLO apparatus 101 according to the present exemplary embodiment will be described. FIGS. 1A and 1B illustrate an example of an entire configuration of the AOSLO apparatus 101 according to the present exemplary embodiment. FIG. 1A is a top view of the AOSLO apparatus of the embodiment, and FIG. 1B is a side view of the AOSLO apparatus 101 of the embodiment. In the present exemplary embodiment, a side of AOSLO apparatus 101 seen from a face rest 104 is a front.

The AOSLO apparatus 101 includes a head unit 102, a stage unit 103, a face rest 104, a liquid crystal monitor 105, a control PC 106, and a joystick 107.

The head unit 102 includes a unit for capturing an image of, for example, a subject's eye, and a main optical system. The included optical system will be described in detail below. In the present exemplary embodiment, the head unit 102 is installed on the stage unit 103. The head unit is an example of a measurement unit.

The stage unit 103 moves the head unit 102 in horizontal and vertical directions according to a subject's operation of the joystick 107. For example, the head unit 102 can be moved in the horizontal direction (X and Z directions) by inclining the joystick 107, and in the vertical direction (Y direction) by rotating the joystick 107.

A face of the subject can be set on the face rest 104, and a position of the subject's eye can be adjusted by moving the face receiver 104. Specifically, the face rest 104 includes a chin rest 108 on which a jaw is mounted, and a chin rest driving unit 109 for moving the chin rest 108 on an electric-powered stage.

The liquid crystal monitor 105, which can display various pieces of information, displays, for example, an operation screen of the AOSLO apparatus 101. In the present exemplary embodiment, the liquid crystal is used for a monitor. However, a monitor is not limited to the liquid crystal. Any type can be used as long as it can display information. The liquid crystal monitor 105 can have a touch panel function.

The control PC 106 controls the entire AOSLO apparatus 101.

The joystick 107 receives an instruction from an inspector. For example, the head unit 102 can be moved in the horizontal direction by inclining the joystick 107, and in the vertical direction by rotating the joystick 107. When the liquid crystal monitor 105 has a touch panel function, and the head unit 102 can be moved by the touch panel, there is no need to install any joystick 107.

The liquid crystal monitor 105 is located on the side face of the head unit 102. Not limited to this, however, the liquid crystal monitor 105 can be located at another position such as the rear surface of the head unit 102. Further, the position of the liquid crystal monitor 105 can be fixed or movable. The control PC 106 is located outside the head unit 102. Not limited to this, however, the control PC 106 can be located in the head unit 102 or the stage unit 103. The joystick 107 is located on the side face of the head unit 102. Not limited to this, however, the joystick 107 can be located at another position such as the rear surface of the head unit 102.

<Configuration of Optical System>

Figure 2:
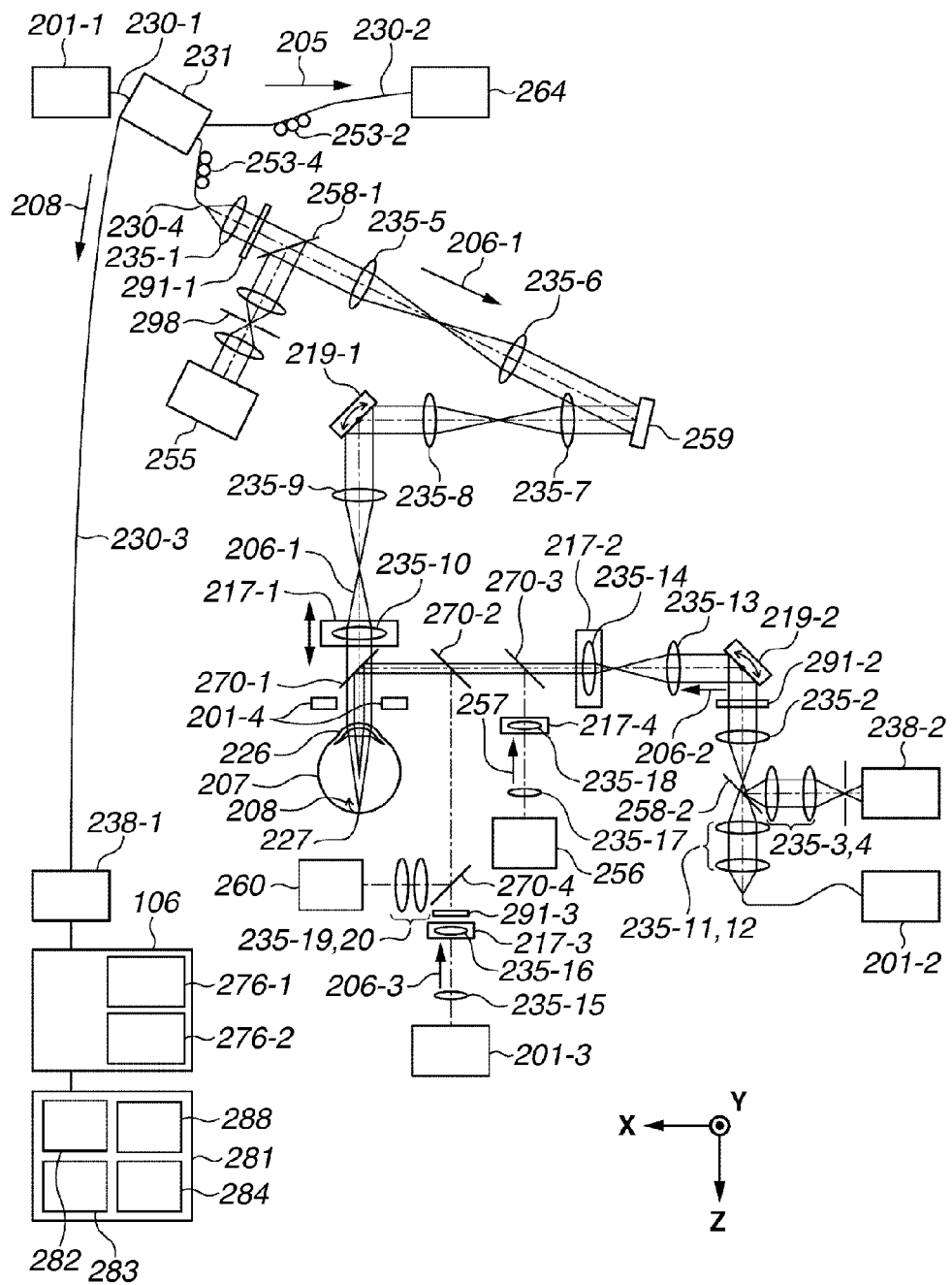
FIG. 2 illustrates an example of a configuration of an optical system of the AOSLO apparatus according to the exemplary embodiment of the present invention.

Next referring to FIG. 2, the optical system included in the head unit 102 will specifically be described. All the optical systems illustrated in FIG. 2 do not need to be included in the head unit 102. For example, the optical systems illustrated in FIG. 2 can be included in the head unit 102 and the stage unit 103. FIG. 2 illustrates an example of a configuration of the optical system of the AOSLO apparatus 101 according to the present exemplary embodiment.

In the present exemplary embodiment, the entire optical system is configured by a refractive optical system using a lens. However, a reflective optical system using a spherical mirror in place of the lens can also be used.

The optical system illustrated in FIG. 2 includes an AOSLO unit, a beacon unit, a WFSLO unit, a fixation lamp unit, and an anterior eye portion observation unit. A plurality of light sources 201-1 to 101-4 included in the AOSLO unit, the beacon unit, the WFSLO unit, the fixation lamp unit, and the anterior eye portion observation unit is an example of a plurality of light sources for emitting measuring beams of different center wavelengths.

The AOSLO unit includes a light source 201-1, single mode fibers 230-1, 230-3, and 230-4, an optical fiber 230-2, an photocoupler 231, polarization controllers 253-2 and 253-24, and a shutter 291-1. The AOSLO unit further includes lenses 235-1, 235-5, 235-6, 235-7, 235-8, 235-9, and 235-10, a beam splitter 258-1, a spatial light modulator 259, and an X-Y scanner 219-1. The AOSLO unit includes a dichroic mirror 270-1, an electric-powered stage 217-1, a light amount measurement apparatus 264, and a detector 238-1.

The beacon unit includes a light source 201-3, lenses 235-5, 235-6, 235-7, 235-8, 235-9, 235-10, 235-15, and 235-16, an X-Y scanner 219-1, a spatial light modulator 259, and a pinhole 298. The beacon unit further includes a shutter 291-3, dichroic mirrors 270-1, 270-2, and 270-4, electric-powered stages 217-1 and 271-3, a beam splitter 258-1, and a wavefront sensor 255.

The WFSLO unit includes a light source 201-2, lenses 235-2, 235-3, 235-4, 235-11, 235-12, 235-13, and 235-14, a beam splitter 258-2, and an X-Y scanner 219-1. The WFSLO unit further includes an electric-powered stage 217-2, dichroic mirrors 270-1, 270-2, and 270-3, a shutter 291-2, and a detector 238-2.

The fixation lamp unit includes a fixation lamp 256, lenses 235-17 and 235-18, dichroic mirrors 270-1, 270-2, and 270-3, and an electric-powered stage 217-4.

The anterior eye portion observation unit includes an anterior eye portion illumination light source 201-4, dichroic mirrors 270-1, 270-2, and 270-4, lenses 235-19 and 235-20, and a charge-coupled device (CCD) camera 260.

<AOSLO Unit>

The AOSLO unit obtains an AOSLO image.

First, the light source 201-1 will be described. The light source 201-1 is a super luminescent diode (SLD) that is a representative low-coherent light source. As an example, a center wavelength of a beam emitted from the light source 201-1 is 840 nm, and a band width (half value full width) is 50 nm. A value of the center wavelength is determined in view of, for example, losses caused by beam absorption of the subject's eye (crystal lens or corpus vitreum). Generally, losses caused by beam absorption are smaller than a proximate wavelength in the vicinity of 840 nm. In this case, the low-coherent light source is selected to obtain a planar image having limited speckle noise. According to the present embodiment, the SLD is selected. However, any type of a light source can be used as long as it can emit a low-coherent beam, and an amplified spontaneous emission (ASE) or the like can also be used. The light source 201-1 is an example of a second light source for emitting a second measuring beam having a center wavelength longer than the center wavelength of a first measuring beam.

For the wavelength, near-infrared light is suitable for eye measurement. Further, a shorter wavelength is desirable because the wavelength affects horizontal resolution of the obtained planar image and, in this case, for example, the wavelength is 840 nm. Other wavelengths can be selected depending on measured portions of the observation target.

The beam emitted from the light source 201-1 is divided into the reference beam 205 and the measuring beam 206-1 at a rate of 90:10 via the single mode fiber 230-1 and the photocoupler 231. Specifically, the beam emitted from the light source 201-1 is divided into the reference beam 205 and the measuring beam 206-1 by the photocoupler 231. The branch ratio by the photocoupler 231 is not limited to this value.

<Reference Beam 205>

Next, an optical path of the reference beam 205 will be described.

The reference beam 205 divided by the photocoupler 231 enters into the light amount measurement apparatus 264 via the optical fiber 230-2 including the polarization controller 253-2 for controlling beam polarization. The light amount measurement apparatus 264 is used for measuring an amount of the reference beam 205 and monitoring an amount of the measuring beam 206-1. For example, when a measured value of the light amount measurement apparatus 264 exceeds a predetermined threshold value, the control PC 106 determines that a safe beam amount is exceeded and limits entry of the beam emitted from the light source 201-1 into the subject's eye.

<Measuring Beam 206-1>

Next, an optical path of the measuring beam 206-1 will be described.

The measuring beam 206-1 divided by the photocoupler 231 is guided to the lens 235-1 via the single mode fiber 230-4 including a polarization controller for controlling beam polarization, and adjusted to be a parallel beam having, for example, a diameter of 4 mm by the lens 235-1. The value of the beam diameter is only an example, and thus in no way limitative. Then, the measuring beam 206-1 reaches the beam splitter 258-1 via the shutter 291-1. The shutter 291-1 can control whether to enter the beam emitted from the light source 201-1 to the subject's eye 207.

The measuring beam 206-1 passes through the beam splitter 258-1 and the lenses 235-5 and 235-6 to enter into the spatial light modulator 259. The beam splitter 258-1 transmits the beam output from the light source 201-1 to the subject's eye 207 and a return beam of the light source 201-1 from the subject's eye 207. Further, the beam splitter 258-1 reflects a beam emitted from the light source 201-3 and returning from the subject's eye 207, toward the wavefront sensor 255. In other words, the beam splitter 258-1 has characteristics of transmitting beams of wavelengths 800 to 880 nm while reflecting beams of other wavelengths.

In the present exemplary embodiment, the reflective spatial light modulator is used as the aberration correction device. However, a transmissive spatial light modulator or a variable shape mirror can also be used.

The spatial light modulator 259 is controlled by the control PC 106 via a spatial light modulator driver 288 in the driver unit 281. In other words, the spatial light modulator driver 288 is electrically connected to the spatial light modulator 259.

The driver unit 281 illustrated in FIG. 2 is located outside the control PC 106. However, the driver unit 281 can be disposed in the control PC 106.

Then, the measuring beam 206-1 is modulated by the spatial light modulator 259, and passed through lenses 235-7 and 235-8 to enter into the mirror of the XY scanner 219-1. For simplicity, the XY scanner 219-1 is illustrated as one mirror. In reality, however, two mirrors are arranged close to each other as an X scanner and a Y scanner, and raster scanning is performed on a retina 227 vertically to the optical axis. A center of the measuring beam 206-1 is adjusted to coincide with a mirror rotational center of the XY scanner 219-1.

The X scanner scans the measuring beam 206-1 in a direction parallel to a plane of paper, and a resonance scanner is used. For example, a driving frequency of the X scanner is about 7.9 kHz. The Y scanner scans the measuring beam 206-1 in a direction vertical to the plane of paper, and a Galvano scanner is used. For example, a driving waveform is a saw-tooth wave, a frequency is about 32 Hz, and a duty ratio is 16%. The driving frequency of the Y scanner is an important parameter for determining a frame rate of a captured AOSLO image.

The XY scanner 219-1 is controlled from the control PC 106 via an optical scanner driver 282 in a driver unit 281. In other words, the optical scanner driver 282 is electrically connected to the XY scanner 219-1.

The measuring beam 206-1 scanned by the XY scanner 219-1 is guided to the subject's eye 207 that is an observation target via the lenses 235-9 and 235-10 and the dichroic mirror 270-1.

The lenses 235-9 and 235-10, which are optical systems for scanning the retina 227, scan the retina 227 with the measuring beam 206-1 with a pupil center of the subject's eye 207 set as a supporting point.

A diameter of the measuring beam 206-1 is 4 mm. However, the beam diameter can be larger to obtain an optical image of higher resolution, and a beam diameter can be less than 4 mm when high resolution is not necessary. In other words, the beam diameter is not limited to 4 mm.

An electric-powered stage 217-1 can be moved in an illustrated arrow direction to move a position of the accompanying focus lens 235-10, thereby adjusting a focus.

The electric-powered stage 217-1 is controlled from the control PC 106 via an electric-powered stage driver 283 in the driver unit 281. In other words, the electric-powered stage driver 283 is electrically connected to the electric-powered stage 217-1. Adjusting the position of the lens 235-10 enables focusing of the measuring beam 206-1 on a predetermined layer of the retina 227 of the subject's eye 207 to perform observation. The apparatus can even deal with refraction abnormality in the subject's eye 207.

The measuring beam 206-1 passed through the lens 235-10 enters into the subject's eye via the dichroic mirror 270-1.

The dichroic mirror 270-1 transmits the beam output from the light source 201-1 to the subject's eye and a beam emitted from the light source 201-1 and returning from the subject's eye. The dichroic mirror 270-1 reflects a beam output from the light source 201-2 toward the subject's eye, a beam emitted from the light source 201-2 and returning from the subject's eye, and a beam emitted from the anterior eye portion illumination light source 201-4 and returning from the subject's eye. The dichroic mirror 270-1 reflects a beam from the fixation lamp 256. Further, the dichroic mirror 270-1 reflects, for example, a half of a beam and transmits a half of a beam with respect to the beam output from the light source 201-3 to the subject's eye, and a beam emitted from the light source 201-3 and returning from the subject's eye. A ratio of reflection and transmission is not limited to 1:1. In other words, the dichroic mirror 270-1 has characteristics of transmitting beams of wavelengths 800 to 880 nm while reflecting a half of the beam and transmitting a half of the beam of wavelengths 750 to 770 nm. The dichroic mirror 270-1 enables separation of the beams emitted from the light source 201-1 and the light source 201-3, and the beam emitted from from the other light sources.

The measuring beam 206-1, which has entered into the subject's eye 207, becomes a return beam 208 by reflection or scattering from the retina 227 to reversely travel on the optical path, and is guided again to the photocoupler 231. Then, the return beam reaches the detector 238-1 via the single mode fiber 230-3. For the detector 238-1, for example, an avalanche photodiode (APD) or a photomultiplier tube (PMT) that is a high-speed and high-sensitive optical sensor is used. However, the detector is not limited to these. The detector 238-1 converts intensity of the return beam 208 into a voltage, and the control PC 106 forms a planar image of the subject's eye 207 by using this voltage signal. In other words, the detector 238-1 is an example of a first acquisition unit for obtaining a first image of the subject's eye. The detector 238-1 uses a return beam of a second measuring beam from the subject's eye, which is aberration-corrected by the spatial light modulator 259 serving as a correction unit. For example, the first image is a fundus image of the subject's eye.

<WFSLO Unit>

Next, the WFSLO unit will be described. The WFSLO unit obtains a WFSLO image. The WFSLO unit has a configuration basically similar to that of the AOSLO unit, and thus description of overlapping portions will be omitted.

The WFSLO unit includes a light source 201-2. The light source 201-2 is a SLD as in the case of the AOSLO unit. A center wavelength of a beam emitted from the light source 201-2 is 920 nm, and a band width is 20 nm. The light source 201-2 is an example of a fourth light source for emitting a fourth measuring beam having a center wavelength longer than the center wavelength of the second measuring beam. According to the present embodiment, the SLD is selected. However, any type of a light source can be used as long as it can emit a low-coherent beam, and amplified spontaneous emission (ASE) may be used. The wavelength and the band width of the beam emitted from the light source 201-2 are not limited to these values. Other values can be employed.

An optical path of a measuring beam 206-2 emitted from the light source 201-2 will be described. The measuring beam 206-2 emitted from the light source 201-2 is guided to the subject's eye 207 via the shutter 291-2, the lens 235-2, the lenses 235-11 to 235-14, the beam splitter 258-2, the XY scanner 219-2, and the dichroic mirrors 270-1 to 270-3. The shutter 291-2 can perform control to determine whether to enter the beam emitted from the light source 201-3 into the subject's eye 207.

The beam splitter 258-2 transmits the beam output from the light source 201-2 to the subject's eye 207 while reflecting a beam emitted from the light source 201-2 and returning from the subject's eye to the detector 238-2.

The dichroic mirror 270-2 transmits the beam output from the light source 201-2 to the subject's eye, a beam emitted from the light source 201-2 and returning from the subject's eye, and a beam from the fixation lamp 256. The dichroic mirror 270-2 reflects a beam output from the light source 201-3 to the subject's eye and a beam emitted from the light source 201-3 and returning from the subject's eye. The dichroic mirror 270-2 reflects a beam output from the anterior eye portion illumination light source 201-4 and returning from the subject's eye 207. In other words, the dichroic mirror 270-2 has characteristics of reflecting beams of wavelengths 700 to 880 nm while transmitting beams of other wavelengths. The dichroic mirror 270-2 enables separation of the beams emitted from the light source 201-3 and the anterior eye portion illumination light source 201-4, from the beams emitted from the light source 201-2 and the fixation lamp 256.

The dichroic mirror 270-3 transmits the beam output from the light source 201-2 to the subject's eye, the beam emitted from the light source 201-2 and returning from the subject's eye, and the beam from the fixation lamp 256. On the other hand, the dichroic mirror 270-3 reflects the beam output from the fixation lamp 256 to the subject's eye. In other words, the dichroic mirror 270-3 has characteristics of transmitting beams of wavelengths of 700 nm or more while reflecting beams of other wavelengths. The dichroic mirror 270-3 enables separation of the beam emitted from the fixation lamp 256, from the beam emitted from the light source 201-2.

In FIG. 2, for simplicity, the XY scanner 219-2 is illustrated as one mirror. In reality, however, two mirrors are arranged close to each other as an X scanner and a Y scanner, and raster scanning is performed on a retina 227 vertically to the optical axis.

The X scanner as a component of the XY scanner 219-2 scans the measuring beam 206-2 in a direction parallel to a plane of paper, and a resonance scanner is used. For example, a driving frequency is about 3.9 kHz. The Y scanner scans the measuring beam 206-2 in a direction vertical to the plane of paper, and a Galvano scanner is used. For example, a driving waveform is a saw-tooth wave, a frequency is about 15 Hz, and a duty ratio is 16%. The driving frequency of the Y scanner is an important parameter for determining a frame rate of the WFSLO image. The XY scanner 219-2 is controlled from the control PC 106 via the optical scanner driver 282 in the driver unit 281. In other words, the optical scanner driver 282 is electrically connected to the XY scanner 219-2.

The optical system is configured so that a diameter of the measuring beam 206-2 is 1 mm. However, the beam diameter can be larger to obtain an optical image of higher resolution, and a beam diameter can be less than 1 mm when high resolution is not necessary. In other words, the beam diameter is not limited to 1 mm.

The measuring beam 206-2, which has entered into the subject's eye 207, is converted into a return beam 208 by reflection or scattering from the retina 227, and reaches the detector 238-2 via the dichroic mirrors 270-1 to 270-3, the lenses 235-13 and 235-14, the lenses 235-2 to 235-4, the XY scanner 219-2, and the beam splitter 258-2. The detector 238-2 is an example of a second light reception unit.

<Beacon Unit>

Next, a beacon unit that measures aberration occurring in the subject's eye 207 will be described.

The beacon unit includes a light source 201-3. The light source 201-3 is an example of a first light source for emitting a first measuring beam. A center wavelength of a beam emitted from the light source 201-3 is 760 nm, and a band width is 20 nm. The wavelength and the band width of the beam emitted from the light source 201-3 are not limited to these values. Other values can be employed.

A measuring beam 206-3 emitted from the light source 201-3 is guided to the subject's eye 207 that is an observation target via the shutter 291-3, the lenses 235-15 and 235-16, and the dichroic mirrors 270-1, 270-2, and 270-4. To prevent reflection from a cornea 226, the measuring beam 206-3 is incident, deviated from, for example, the center of the subject's eye 207. The shutter 291-3 can perform control to determine whether to enter the beam emitted from the light source 201-3 into the subject's eye 207.

The dichroic mirror 270-4 transmits the beam output from the light source 201-3 to the subject's eye 207 while it reflects a beam emitted from the anterior eye portion illumination light source 201-4 and returning from the subject's eye, toward the CCD camera 260. In other words, the dichroic mirror 270-4 has characteristics of transmitting beams of wavelengths of 750 nm or more while reflecting beams of other wavelengths. The dichroic mirror 270-4 enables separation of the beam emitted from the anterior eye portion illumination light source 201-4, from the beam emitted from the light source 201-3.

A part of the return beam 208 of the light source 201-3 enters into the wavefront sensor 255 via the beam splitter 258-1 and the pinhole 298, and aberration of the return beam 208 occurring in the subject's eye is measured. In other words, the wavefront sensor 255 is an example of an aberration measurement unit for measuring aberration caused by the subject's eye by using the return beam of the first measuring beam from the subject's eye. The wavefront sensor 255 is also an example of a first light reception unit. The pinhole 298 is provided for the purpose of blocking off unnecessary beams other than the return beam 208. The wavefront sensor 255 is electrically connected to the control PC 106.

The wavefront sensor 255 is a Shack-Hartman wavefront sensor, and a measurement range is −10 D to +5 D. The acquired aberration is expressed by using Zernike polynomial, which indicates aberration at the subject's eye 207. The Zernike polynomial includes a tilt term, a defocus term, an astigmatism term, a coma term, and a trefoil term.

The lenses 235-5 to 235-10 are arranged such that the cornea 226, the XY scanner 219-1, the wavefront sensor 255, and the spatial light modulator 259 can be optically conjugate with one another. Thus, the wavefront sensor 255 can measure the aberration caused by the subject's eye 207. The spatial light modulator 259 can correct the aberration caused by the subject's eye 207.

<Fixation Lamp>

A light flux 257 from the fixation lamp 256 has a role in prompting fixation or rotation of the subject's eye 207. In other words, the fixation lamp 256 is an example of a fixation lamp for guiding a direction of a line of sight of the subject's eye.

Figure 3:
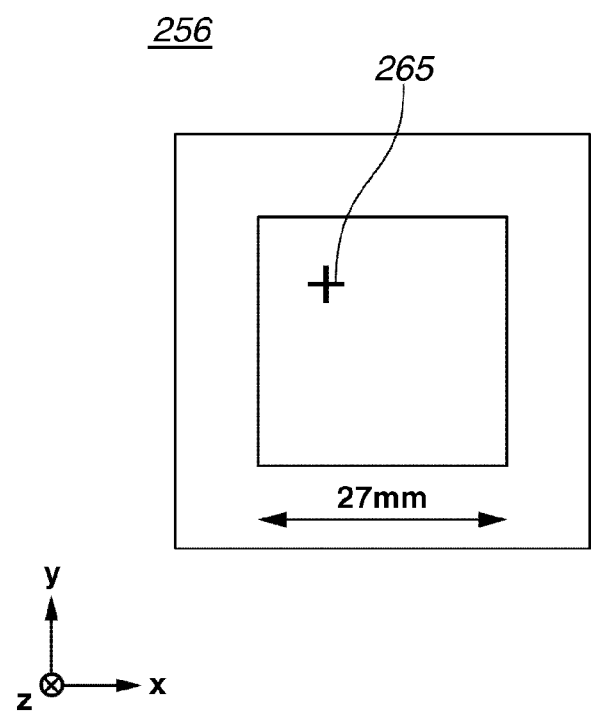
FIG. 3 illustrates an example of a fixation lamp according to the exemplary embodiment of the present invention.
Figure 4:
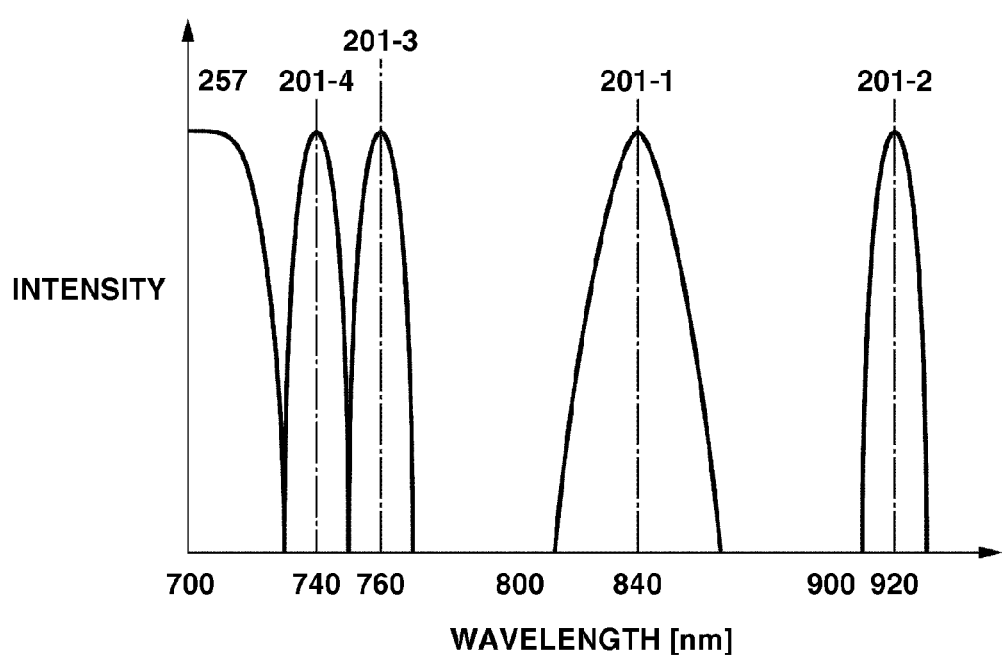
FIG. 4 illustrates an example of a wavelength distribution of a measuring beam of the AOSLO apparatus according to the exemplary embodiment of the present invention.

The fixation lamp 256, which includes a light emitting display module, has a display surface (27 mm, 128×128 pixels) on an XY plane. A liquid crystal, an organic electroluminescence (EL) or a light emitting diode (LED) array can be used. The subject's eye 207 pays close attention to the light flux 257 from the fixation lamp 256, so that fixation or rotation of the subject's eye 207 is prompted. In the display surface of the fixation lamp 256, for example, as illustrated in FIG. 3, a cross pattern blinks at an arbitrary lighting position 265. The light flux 257 emitted from the fixation lamp 256 is a visible beam. As illustrated in FIG. 4, a waveform of a part of the light flux 256 (e.g., red waveform included in the visible beam) is equal to or more than 700 nm.

The light flux 257 from the fixation lamp 256 is guided to the retina 227 via the lenses 235-17 and 18 and the dichroic mirrors 270-1 to 270-3. The lenses 235-17 and 235-18 are arranged such that the display surface of the fixation lamp 256 and the retina 227 can be optically conjugate with each other. The fixation lamp 256 is controlled from the control PC 106 via a fixation lamp driver 284 in the driver unit 281. The fixation lamp driver 284 is electrically connected to the fixation lamp 256.

A size of the display surface of the fixation lamp 256 and the number of pixels are not limited to the aforementioned values. Other values can be employed. In the above example, the cross fixation pattern is employed. Not limited to this, however, other shapes can be employed.

<Anterior Eye Portion Observation Unit>

Next, the anterior eye portion observation unit will be described. The anterior eye portion observation unit obtains an anterior eye portion image of the subject's eye.

The anterior eye portion observation unit 201-4 is a LED having, for example, a center wavelength of 740 nm. For example, a band width is several tens of nm. The center wavelength and the band width are not limited to these values. In other words, the anterior eye portion observation unit 201-4 is an example of a third light source for emitting a third measuring beam having a center wavelength shorter than that of the second measuring beam. A beam emitted from the anterior eye portion observation unit 201-4 illuminates the subject's eye 207, and its reflected beam enters into the CCD camera 260 via the dichroic mirrors 207-1, 207-2, and 207-4 and the lenses 235-19 and 235-20.

<Focus and Astigmatism Correction>

As described above, the optical system in the head unit 102 includes the AOSLO unit, the WFSLO unit, the beacon unit, the fixation lamp unit, and the anterior eye portion observation unit. The AOSLO unit, the WFSLO unit, the beacon unit, and the fixation lamp unit individually include the electric-powered stages 217-1 to 217-4, and the four electric-powered stages are moved interlocking with each other. However, in a case where focus positions are to be individually adjusted, the positions can be adjusted by individually moving the electric-powered stages.

The lens 235-10 can be replaceable, and a spherical lens or a cylindrical lens can be used according to the aberration (refractive abnormality) caused by the subject's eye 207. Not limited to one lens, a plurality of lenses can be installed in combination.

<Shutter>

The AOSLO unit, the WFSLO unit, and the beacon unit include shutters 291-1 to 291-3 on the optical paths of the light sources 201-1 to 201-3, and whether to enter a beam into the subject's eye 207 can be controlled by individually blocking off beams. Opening or closing of the shutters 291-1 to 291-3 is controlled by the control PC 106.

In the present exemplary embodiment, the shutter is used for controlling the beam which enters into the subject's eye 207. Not limited to this, however, the beam entering into the subject's eye 207 can be controlled by changing the optical path by a mirror or the like. The beam entering into the subject's eye 207 can be controlled by directly turning ON/OFF the light sources 201. Incidence and limitation of incidence on the subject's eye 207 can be switched by disposing an attenuation filter in place of the shutter and inserting or pulling it out in/from the optical path. Similarly, the anterior segment observation unit and the fixation lamp unit can be controlled by turning ON/OFF the light source 201-4 and a light-emitting display module. When the shutters 291-1 to 291-3 are used, the entry of a beam into the subject's eye can be controlled while the light sources 201-1 to 201-3 are kept lit. Thus, when the incidence limitation of the measuring beam on the subject's eye 207 is cancelled, no time is taken from turning-OFF of the light sources 201-1 to 201-3 to stable beam emission, enabling quick control. Similar effects can be obtained also when the mirror or the filter is used.

Figure 7:
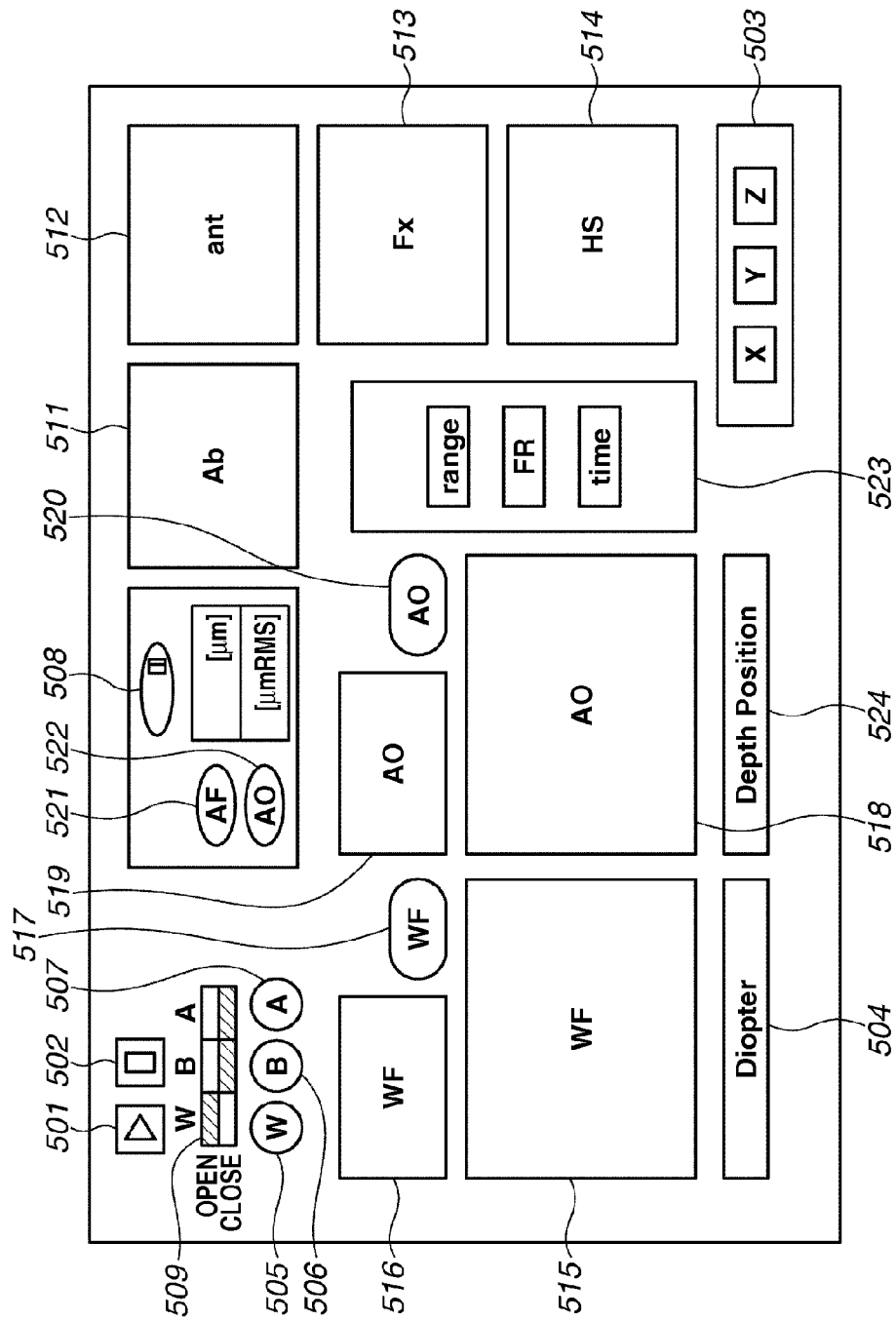
FIG. 7 illustrates an example of a configuration of a control software screen of the AOSLO apparatus according to the exemplary embodiment of the present invention.

The opened/closed state of the shutters 291-1 to 291-3 is displayed in a shutter state display region 509 of a control software screen illustrated in FIG. 7. By displaying the opened/closed state of the shutter, the inspector can clearly and easily know which of the measuring beams 206-1 to 206-3 is being applied to the subject's eye 207. As a result, certainty of an imaging operation can be increased.

<Wavelength of Each Light Source>

FIG. 4 illustrates an example of a wavelength distribution of the light sources used for the AOSLO unit, the WFSLO unit, the beacon unit, the fixation lamp unit, and the anterior eye portion observation unit. To enable the dichroic mirrors 270-1 to 270-4 to divide the beams, different wavelength ranges are set.

To reduce dazzling of the subject's eye, the beams emitted from the light sources 201-1 to 201-4 are desirably infrared beams having wavelengths of 700 nm or more. High image quality is not required of the light source 201-3 of the beacon unit. Only a Hartman image must be obtained. Accordingly, a beam amount can be smaller than those of the light sources 201-1 and 201-2. Thus, an influence of the wavelength of the beam emitted from the light source 201-3 on the subject being inspected is relatively small even when it is near a visible light region, and the wavelength of the beam emitted from the light source 201-3 can be near the visible light region. Sensors normally used for the detectors 238-1 and 238-2 are silicon sensors. Since sensitivity of the silicon sensor is extremely low near 1000 nm, the wavelengths of the beams emitted from the light sources 201-1 to 201-4 are desirably equal to less than 1000 nm. The AOSLO apparatus 101 configured to obtain the AOSLO image uses the WFSLO image which assists in obtaining the desired AOSLO image. Thus, to obtain a desired end AOSLO image with high resolution, the wavelength of the beam emitted from the light source 201-1 is set shorter than that of the beam emitted from the light source 201-2. As described above, a center wavelength of the light source 201-1 is desirably set near 840 nm based on eye characteristics.

It is therefore advised that in the case of the AOSLO apparatus 101 for fundus observation, the beacon unit, the AOSLO unit, and the WFSLO unit be arranged in this order from the short wavelength side, and center wavelengths be spaced from each other to facilitate separation by the dichroic mirror.

An anterior eye portion image emitted from the anterior eye portion imaging light source 201-4 is used for initial alignment of the head unit 201. The alignment of the head unit 201 is performed while watching the WFSLO image. On the other hand, the beam emitted from the light source 201-3 is used for measuring aberration necessary for obtaining the desired end ALSO image with high resolution. Accordingly, since the beam amount of the light source 201-3 is set larger than that of the anterior eye portion imaging light source 201-4 to accurately measure the aberration, by setting the wavelength of the light source 201-3 longer than that of the anterior eye portion imaging light source 201-4, the aberration can be accurately measured while reducing a burden on the subject. Specifically, a center wavelength of the third measuring beam is equal to more than 700 nm, and center wavelengths of the second and fourth measuring beams are equal to less than 1000 nm. Since it is only necessary to obtain the anterior eye portion image used for the initial alignment of the head unit 201, the beam amount of the anterior eye portion imaging light source 201-4 can be smaller than those of the other light sources. When the center wavelength of the anterior eye portion imaging light source 201-4 and the center wavelength of the light source 201-2 are switched, the center wavelength of the light source 201-2 that emits a beam scanned on the subject's eye approaches that of the visible beam. Consequently, the subject's eye follows a track of the beam during scanning, which destabilizes fixation. Thus, the center wavelength of the anterior eye portion imaging light source 201-4 and the center wavelength of the light source 201-2 are set to the above conditions.

An interval between the center wavelengths is desirably double or more of the sum of ½ of half-value full widths of adjacent light sources. In the present exemplary embodiment, an interval between the center wavelengths of the light source 201-1 and the light source 201-2 is 80 nm, and an interval between the center wavelengths of the light source 201-1 and the light source 201-3 is also 80 nm. Half-value full widths of the light sources 201-1 to 201-3 are respectively 50 nm, 20 nm, and 20 nm. Accordingly, double the sum of ½ of half-value full widths of the light source 201-1 and the light source 201-2 is 70 nm, double the sum of ½ of half-value full widths of the light source 201-1 and the light source 201-3 is also 70 nm, and a interval between the center wavelengths is set larger than these values. Thus, beam losses at the respective light sources can be reduced as much as possible. Hereinafter, a wavelength determination method including a wavelength determination step will specifically be described. When a wavelength distribution is generally Gaussian distribution, a width of the Gaussian distribution at a position of ½ of a peak (intensity peak) of the Gaussian distribution is a half-value full width, and intensity at a position double the half-value full width is 1/16 of the peak value of the Gaussian distribution. In other words, 95% or more of the entire beam amount is included in a portion where the width of the Gaussian distribution is less than double the half-value full width. Thus, by setting the interval between the center wavelengths double or more of the sum of ½ of half-value full widths of the adjacent light sources as described above, overlapping of the wavelengths between the light sources can be made difficult. When the interval between the center wavelengths is set double ½ of half-value full widths of the adjacent light sources, the interval between the center wavelengths can be reduced while preventing overlapping of the wavelengths between the light sources. Thus, the wavelengths can be effectively used. As a result, a wavelength as short as possible can be used to improve resolution.

In the aforementioned example, the interval between the center wavelengths is set double or more of ½ of half-value full widths of the adjacent light sources. However, the interval is not limited to this. For example, the interval between the center wavelengths can be set n times larger than the sum of 1/n of half-value full widths of the adjacent light sources, where n is a natural number. In the aforementioned example, n is 2. In other words, the interval between the adjacent center wavelengths is a value n times larger than the sum of 1/n of half-value full widths of a plurality of adjacent measuring beams. Specifically, the interval between the adjacent center wavelengths is a value n times larger than the sum of 1/n of half-value full widths of the plurality of adjacent measuring beams. With respect to the second measuring beam emitted from the light source 201-1 and the first measuring beam emitted from the light source 201-3, an interval between the center wavelength of the first measuring beam and the center wavelength of the second measuring beam is a value based on the respective half-value full widths of the first measuring beam and the second measuring beam. An interval between the center wavelength of the first measuring beam and the center wavelength of the second measuring beam is a value based on a value n times larger than the sum of a value 1/n of the respective half-value full widths of the first measuring beam and the second measuring beam. Further, an interval between the center wavelength of the first measuring beam and the center wavelength of the second measuring beam is a value n times larger than the sum of a value 1/n of the respective half-value full widths of the first measuring beam and the second measuring beam.

The wavelength width used for determining the interval between the center wavelengths may not be a half-value full width. An arbitrary wavelength width can be used. For example, a wavelength width half of the half-value full width can be used from the start to omit the division, or a wavelength width near the half-value full width can be used. In other words, the interval between the adjacent center wavelengths can be determined based on the respective wavelength widths of the plurality of adjacent measuring beams.

Further, when the interval between the adjacent center wavelengths is set double ½ of half-value full widths of the adjacent light sources, overlapping of the wavelengths between the light sources is greater than that when the interval between the center wavelengths is set double or more of the sum of ½ of half-value full widths of the adjacent light sources. In this case, an attenuation filter for reducing an influence of the wavelength overlapping may be provided, and thus the influence of the wavelength overlapping can be reduced. For example, the narrower the interval between the center wavelengths, the larger the wavelength-overlapped portions. Thus, an attenuation filter for attenuating wavelengths of a wider range may be used, as the interval between the center wavelengths becomes narrower. A table associating the interval between the center wavelengths with an attenuation wavelength range is prepared, and by referring to the table, the control PC 106 inserts or pulls out the attenuation filter (not illustrated) into/from an arbitrary position of the optical path, for example, in front of the subject's eye 207 or in each light source. The use of such an attenuation filter can bring the center wavelengths closer to each other. As a result, the wavelengths can be more effectively used.

An interval between the center wavelength of the light source 201-3 and the center wavelength of the light source 201-4 can be determined or does not need to be determined by a method similar to the aforementioned method. The interval between the center wavelengths does not need to be determined because the anterior eye portion image does not need accuracy as high as the other images.

FIG. 4 does not define intensity or spectral shapes but illustrates a difference in wavelength between the light sources.

<Image Formation>

Next, a configuration method of a captured mage will be described.

When the beam enters the detector 238-1, its intensity is converted into a voltage. A voltage signal obtained at the detector 238-1 is converted into a digital value at an AD board 276-1 in the control PC 106. The control PC 106 performs data processing in synchronization with an operation or a driving frequency of the XY scanner 219-1 to form an AOSLO image. A capturing speed of the AD board 276-1 is 15 MHz. Similarly, a voltage signal acquired at the detector 238-2 is converted into a digital value at an AD board 276-2 in the control PC 106, and a WFSLO image is formed by the control PC 106. In other words, the detector 238-2 is an example of a third acquisition unit for obtaining, by using a return beam of the fourth measuring beam from the subject's eye, a second image of the subject's eye used for determining an acquisition position of a first image in the subject's eye. For example, the second image is a fundus image of the subject's eye having a field angle wider than that of the first image.

<Control PC>

Figure 5:
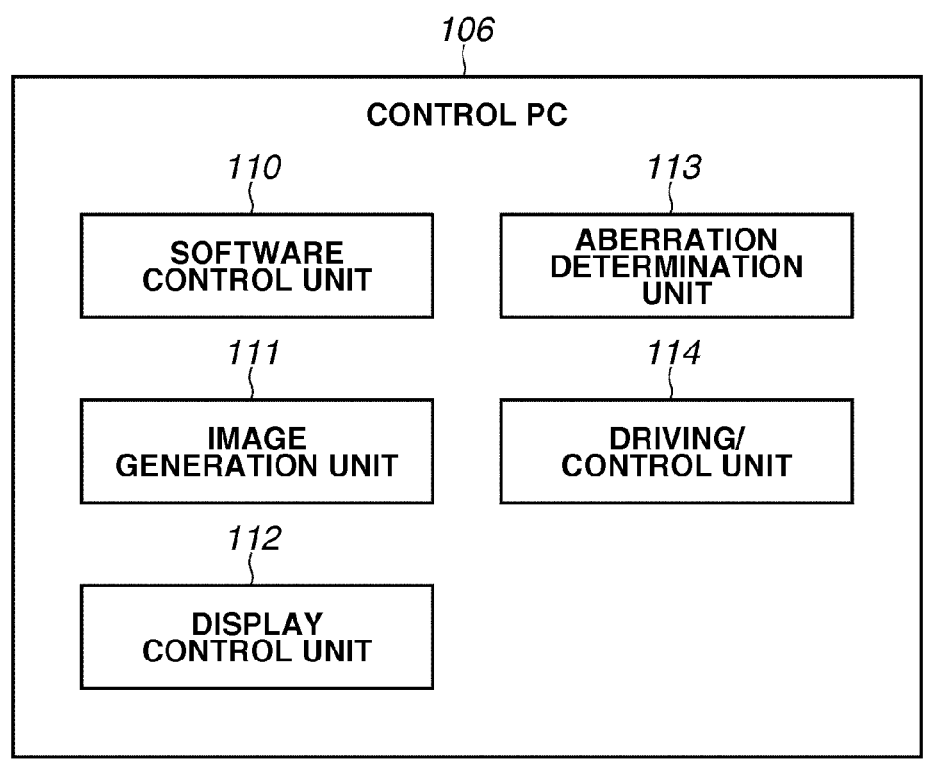
FIG. 5 schematically illustrates an example of a function of a control personal computer (PC).

An example of a function of the control PC 106 will be described. FIG. 5 schematically illustrates the example of the function of the control PC 106.

The control PC 106 functions as a software control unit 110, an image generation unit 111, a display control unit 112, an aberration determination unit 113, and a driving/control unit 114 by executing a predetermined program stored in a storage device such as a memory with a processing unit such as a central processing unit (CPU).

The software control unit 110 controls activation or stopping of measurement control software and viewer software. For example, the software control unit 110 activates the measurement control software when power is turned ON for the AOSLO apparatus 101 or when an inspector specifies a control software execution file. The software control unit 110 activates the viewer software when the inspector specifies a viewer software execution file. The software control unit 110 stops the measurement control software and the viewer software when the inspector instructs an end of the software. The control software and the viewer software can be stored in a storage unit such as a memory included in the control PC 106, or in an external storage unit communicable with the control PC 106 by wireless or wire.

The image generation unit 111 generates various images. For example, the image generation unit 111 generates an AOSLO image based on an output of the AD board 276-1. The image generation unit 111 generates a WFSLO image based on an output of the AD board 276-2. The image generation unit 111 generates a Hartman image based on an output of the wavefront sensor 255. The image generation unit 111 generates an anterior eye portion image based on an output of the CCD camera 260. In other words, the CCD camera 260 is an example of a second acquisition unit for obtaining an anterior eye portion image of the subject's eye used for alignment.

The display control unit 112 displays various pieces of information such as the images generated by the image generation unit 111 on the liquid crystal monitor 105. The display control unit displays a graph or values of aberrations determined by the aberration determination unit 113 on the liquid crystal monitor 105.

The display control unit 112 further displays opened/closed states of the shutters 291-1 to 291-3 in a shutter state display region 509.

The information displayed in the shutter state display region 509 is not limited to the shutter opened/closed state. Any information indicating the incident state of the measuring beam on the subject's eye can be used. For example, information indicating insertion or separation of a filter in/from the optical path can be displayed when the filter is used in place of the shutter, or information indicating incidence of a measuring beam can be displayed.

The aberration determination unit 113 determines aberration of the subject's eye 207 based on an output of the wavefront sensor 255. Specifically, the aberration determination unit 113 determines aberration of the subject's eye 207 based on the Hartman image.

The driving/control unit 114 drives various movable members. Specifically, the driving/control unit 114 drives the XY scanners 219-1 and 219-2 via the optical scanner driver 282. The driving/control unit 114 drives the electric-powered stages 217-1 to 217-4 via the electric-powered stage driver 283. Further, the driving/control unit 114 drives the fixation lamp 256 via the fixation lamp driver 284. Specifically, the driving/control unit 114 controls movement of a lighting position 265, switching between lighting and blinking, and changing of a size or a shape. The driving/control unit 114 controls the spatial light modulator 259 via the spatial light modulator driver 288. Specifically, the driving/control unit 114 controls the spatial light modulator 259 based on the aberration determined by the aberration determination unit 113, thereby correcting the aberration at the subject's eye. More specifically, the driving/control unit 114 controls the spatial light modulator 259 to reduce the aberration. In other words, the spatial light modulator 259 is an example of a correction unit for correcting aberration of a return beam from the subject's eye, of the second measuring beam generated by the subject's eye based on the aberration measured by the aberration measurement unit.

Further, the driving/control unit 114 drives a chin rest 108 via a chin rest driving unit 109 according to an inspector's input.

The driving/control unit 114 controls opening/closing of the shutters 291-1 to 291-3. Further, the driving/control unit 114 controls turning ON or OFF of the light source.

<Imaging Procedure>

Figure 6:
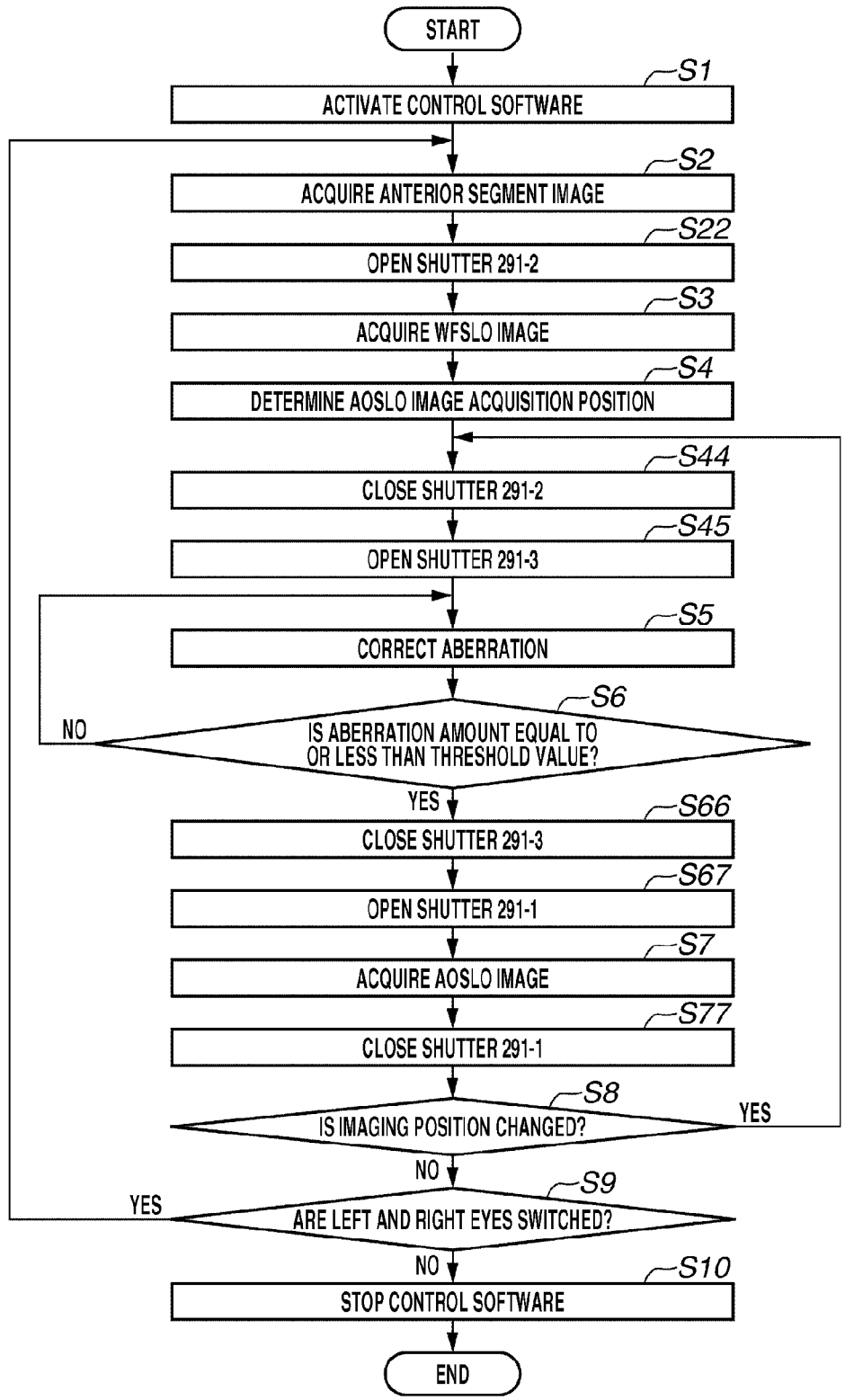
FIG. 6 is a flowchart illustrating an example of an imaging procedure by the AOSLO apparatus according to the exemplary embodiment of the present invention.

Next, referring to flowcharts of FIGS. 6 and 7, an imaging procedure in the AOSLO apparatus 101 of the present exemplary embodiment will be described. FIG. 6 is a flowchart illustrating an example of an operation of the AOSLO apparatus according to the exemplary embodiment. FIG. 7 illustrates an example of a control screen of the AOSLO apparatus 101 displayed on the liquid crystal monitor 105 according to the exemplary embodiment.

Hereinafter, each step of the flowchart will be described in detail. In an initial state, the shutters 291-1 to 291-3 are all closed.

When power of the AOSLO apparatus 101 is turned ON including the control PC 106, each processing of the AOSLO apparatus 101 is started.

[Step S1]

When power of the AOSLO apparatus 101 is turned ON including the control PC 106, the software control unit 110 activates the measurement control software. When the measurement control software is activated, the display control unit 112 displays the control software screen illustrated in FIG. 7 on the liquid crystal monitor 105. The subject sets a face on the face rest 104 after the measurement control software has been activated.

An example of the control screen illustrated in FIG. 7 will be described. A screen configuration of the control software illustrated in FIG. 7 is only an example, and thus in no way limitative. In other words, arrangement or the like of the control screen can be arbitrarily changed.

The control screen illustrated in FIG. 7 includes an execution button 501, a stop button 502, an electric-powered stage button 503, a focus adjustment button 504, a WFSLO measurement button 505, an aberration measurement button 506, and an AOSLO measurement button 507.

The control screen illustrated in FIG. 7 includes an aberration correction temporary stop button 508, a shutter state display region 509, an aberration display region 511, an anterior eye portion display region 512, a fixation lamp position display region 513, a wavefront display region 514, and a WFSLO display region 515.

The control screen illustrated in FIG. 7 includes a WFSLO intensity display region 516, a WFSLO recording button 517, an AOSLO display region 518, an AOSLO intensity display region 519, an AOSLO recording button 520, and an autofocus button 521.

The control screen illustrated in FIG. 7 further includes an aberration correction button 522, an imaging condition setting button 523, and a depth adjustment button 524.

After the execution button 501 has been selected (e.g., clicked) by an instruction unit such as a mouse, the driving/control unit 114 lights the anterior eye portion illumination light source 201-4, and a beam emitted from the anterior eye portion illumination light source 201-4 enters into the subject's eye 207. Then, the display control unit 112 displays an anterior eye portion image generated based on an output of the CCD camera 260 in the anterior eye portion display region 512.

When the execution button 501 is selected, the control PC 106 can display a screen for selecting or registering patient information on the liquid crystal monitor 105. In this case, after the patient information has been selected or registered, the anterior eye portion illumination light source 201-4 can be lit, and the display control unit 112 can display the anterior eye portion image in the anterior eye portion display region 512. The selection by the instruction unit is not limited to clicking. When the liquid crystal monitor 105 has a touch panel function, the inspector can perform selection by touching the monitor.

When the stop button 502 is selected, the software control unit 110 stops the control software.

The electric-powered stage movement button 503 includes an X stage movement button, a Y stage movement button, and a Z stage movement button. When the electric-powered stage movement button 503 is selected, the driving/control unit 114 moves the chin rest 108 via the chin rest driving unit 109. For example, each of the X stage movement button, the Y stage movement button, and the Z stage movement button is a slider, and the driving/control unit 114 moves the chin rest 108 according to a moving amount and a moving direction of the slider. For example, when the Y stage button is selected, the driving/control unit 114 moves the chin rest 108 in a Y direction. Similarly, the driving/control unit 114 moves the chin rest 108 in an X direction and a Y direction according to selected buttons. The electric-powered stage movement button 503 is not limited to the slider. Any other form can be employed as long as the chin rest 108 can receive an driving instruction.

For example, the focus adjustment button 504 is a slider. The driving/control unit 114 drives the lenses 235-10, 235-14, 235-16, and 235-18 according to a moving amount and a moving direction of the slider. The focus adjustment button 504 is not limited to the slider. Any other form can be employed as long as the lenses 235-10, 235-14, 235-16, and 235-18 can receive a driving instruction.

When the WFSLO measurement button 505 is selected, the control PC 106 permits the beam emitted from the light source 201-1 to enter into the subject's eye. Specifically, entry of the beams emitted from the light sources 201-1 to 201-3 into the subject's eye is limited before selection of the WFSLO measurement button 505. After the selection, the beam emitted from the light source 201-2 can enter into the subject's eye. This switching of the state is carried out, for example, by the driving/control unit 114 lighting the turned-OFF light source 201-2 or retreating the shutter inserted into the optical path connecting the subject's eye with the light source 201-2.

When the aberration measurement button 506 is selected, the driving/control unit 114 limits entry of the beam emitted from the light source 201-2 into the subject's eye 207. The entry of the emitted beam into the subject's eye 207 is limited by, for example, closing the shutter 291-2 of the optical path connecting the subject's eye 207 with the light source 201-2 or turning OFF the light source 201-2. When the aberration measurement button 506 is selected, the control PC 106 permits the beam emitted from the light source 201-3 to enter into the subject's eye 207. Specifically, entry of the beams emitted from the light sources 201-1 and 201-3 into the subject's eye is limited before the aberration measurement button 506. After the selection, the beam emitted from the light source 201-3 enters into the subject's eye. This switching of the state is carried out, for example, by the driving/control unit 114 lighting the turned-OFF light source 201-3 or opening the shutter 291-3 inserted into the optical path connecting the subject's eye 207 with the light source 201-3. Either of the limitation of the entry of the beam emitted from the light source 201-2 into the subject's eye 207 and the permission of the entry of the beam emitted from the light source 201-3 into the subject's eye 207 can be executed first, or both can be simultaneously executed. However, it is desirable that in order to limit the increase of a beam amount entering into the subject's eye 207 as much as possible, after the entry of the beam emitted from the light source 201-2 into the subject's eye 207 is limited, the entry of the beam emitted from the light source 201-3 into the subject's eye 207 is permitted.

When the AOSLO measurement button 507 is selected, the driving/control unit 114 limits entry of the beam emitted from the light source 201-3 into the subject's eye. The entry of the emitted beam into the subject's eye 207 is limited by, for example, closing the shutter 291-3 of the optical path connecting the subject's eye 207 with the light source 201-3 or turning OFF the light source 201-3. When the AOSLO measurement button 507 is selected, the control PC 106 permits the beam emitted from the light source 201-2 to enter into the subject's eye 207. Specifically, entry of the beams emitted from the light sources 201-1 and 201-2 into the subject's eye 207 is limited before the AOSLO measurement button 507 is selected. After the selection, the beam emitted from the light source 201-1 enters into the subject's eye 207. This switching of the state is carried out, for example, by the driving/control unit 114 lighting the turned-OFF light source 201-1 or opening the shutter 291-1 inserted into the optical path connecting the subject's eye 207 with the light source 201-1. Either of the limitation of the entry of the beam emitted from the light source 201-3 into the subject's eye 207 and the permission of the entry of the beam emitted from the light source 201-1 into the subject's eye 207 can be executed first, or both can be simultaneously executed. However, it is desirable that in order to limit the increase of a beam amount entering into the subject's eye 207 as much as possible, after the entry of the beam emitted from the light source 201-3 into the subject's eye 207 is limited, the entry of the beam emitted from the light source 201-1 into the subject's eye 207 is permitted.

When the aberration correction temporary stop button 508 is selected, the control PC 106 temporarily stops aberration correction. For example, while the aberration determination unit 113 continues aberration correction, the control of the spatial light modulator 259 by the driving/control unit 114 is stopped. Alternatively, the aberration correction itself is stopped. A resume button can be disposed, and the aberration correction can be resumed when the resume button is selected. Alternatively, when the aberration correction temporary stop button 508 is selected again, the aberration correction can be resumed.

In the shutter state display region 509, information indicating opened/closed states of the shutters 291-1 to 291-3 is displayed by the display control unit 112. In the example illustrated in FIG. 7, with respect to the shutters 291-1 to 291-3, regions indicating an opened state (OPEN in the drawing) of the shutter and a closed state (CLOSE in the drawing) of the shutter are formed. The regions are displayed with emphasis according to the opened/closed states of the shutters 291-1 to 291-3. For example, FIG. 7 illustrates an opened state of the shutter 291-1 and closed states of the shutters 291-2 and 291-3. However, the form of the shutter state display region 509 is not limited to this. Any other display forms can be employed as long as the opened/closed states of the shutters 291-1 to 291-3 can be confirmed. For example, switches corresponding to the shutters 291-1 to 291-3 can be displayed. In this case, the switch is pressed when the shutter is opened while the switch is not pressed when the shutter is closed.

In the aberration display region 511, the aberration determined (calculated) by the aberration determination unit 113 is displayed as a time-sequential graph by the display control unit 112.

In the anterior eye portion display region 512, the anterior eye portion image generated by image generation unit 111 based on the output of the CCD camera 260 is displayed by the display control unit 112.

In the fixation lamp display region 513, information indicating a fixation position is displayed by the display control unit 112. For example, in the fixation lamp display region 513, a grid indicating fixation coordinates is displayed, and the fixation position is displayed as a bright spot on the grid. When the operation unit selects a certain point on the grid, the driving/control unit 114 changes a lighting position 265 in the fixation lamp 256 according to the selected position. In the fixation lamp display region 513, coordinates indicating a current fixation position can be displayed as numerical values. In this case, the lighting position 265 can be changed by changing the displayed numerical values.

In the wavefront display region 514, a Hartman image detected by the wavefront sensor 255 is displayed by the display control unit 112. The wavefront display region 514 can be always provided, or popped up as another window when the aberration measurement button 506 is selected, aberration measurement is started, and a Hartman image is obtained. The pop-up configuration enables effective use of the screen of the liquid crystal monitor 105 when aberration is not being measured.

In the WFSLO display region 515, a WFSLO image generated by the image generation unit 111 is displayed by the display control unit 112.

In the WFSLO intensity display region 516, signal intensity of the WFSLO image is displayed by the display control unit 112. More specifically, the signal intensity of the WFSLO image is displayed as a time-sequential graph.

When the WFSLO recording button 517 is selected, the driving/control unit 114 records the WFSLO image in a storage unit (not illustrated) such as a hard disk drive (HDD).

In the AOSLO display region 518, an aberration-corrected AOSLO image is displayed by the display control unit 112.

In the AOSLO intensity display region 519, signal intensity of the AOSLO image is displayed by the display control unit 112. More specifically, the signal intensity of the AOSLO image is displayed as a time-sequential graph.

When the AOSLO recording button 520 is selected, the driving/control unit 114 records the AOSLO image in a storage unit (not illustrated) such as a HDD.

When the autofocus button 521 is selected, the driving/control unit 114 automatically adjusts positions of the lenses 235-10, 235-14, 235-16, and 235-18 so that a defocus value becomes small.

When the aberration correction button 522 is selected, the driving/control unit 114 automatically adjusts the spatial light modulator 259 so that an aberration amount becomes smaller.

The imaging condition setting button 523 includes, for example, an imaging field angle setting button, a frame rate setting button, and an imaging time setting button. For example, the imaging field angle setting button includes a plurality of buttons corresponding to a plurality of field angles. The inspector can perform imaging with a desired field angle by selecting a button corresponding to the desired field angle. The frame rate setting button and the imaging time setting button are configured as in the case of the imaging field angle setting button.

The depth adjustment button 524 is, for example, a slider. The driving/control unit 114 drives the lens 235-10 according to a moving amount and a moving direction of the slider. The depth adjustment button 524 is not limited to the slider. Any other forms can be employed as long as the lens 235-10 can be driven.

In the aberration display region 525, an aberration amount of a defocus component (μm) and all aberration amounts (μm RMS) determined by the aberration determination unit 113 are displayed by the display control unit 112. Only one of both may be displayed. The units of the displayed aberration amounts are not limited to these units. Other units can be used.

Hereinafter, description will return to the flowchart of FIG. 6.

[Step S2]

When the execution button 501 on the control software screen is pressed, an image of the anterior eye portion is displayed in the anterior eye portion display region 512. When a center of a center of a pupil is not correctly displayed at a screen center, the head portion 102 is moved to a roughly correct position by using the joystick 107. When further adjustment is necessary, the electric-powered stage button 503 on the control screen is pressed, and the chin rest 108 is slightly moved by the driving/control unit 114.

[Step S22]

The driving/control unit 114 opens the closed WFSLO shutter 291-2. In the shutter state display region 509, the opened state of the WFSLO shutter 291-2 is displayed. In the shutter state display region 509, closed states of the shutters 291-1 and 291-3 are displayed.

The WFSLO shutter 291-2 can be opened when the execution button 501 of the control software screen is selected, when the control software is activated, or when the image of the anterior eye portion is displayed in the anterior eye portion display region 512.

[Step S3]

When the image of the anterior eye portion is displayed in a roughly correct state, a WFSLO image is displayed in the WFSLO display region. For example, the inspector sets the fixation at a center position of a fixation lamp position display region 513, and guides a line of sight of the subject's eye 207 to the center. For example, the WFSLO measurement button 505 is automatically selected when the control software is activated or when the execution button 501 is selected.

Then, while watching intensity of the WFSLO image displayed in a WFSLO intensity display region 516, the inspector adjusts the focus adjustment button 504 to increase WFSLO intensity. In the WFSLO intensity display region 516, signal intensity detected by the WFSLO unit is time-sequentially displayed with a horizontal axis indicating time and a vertical axis indicating signal intensity. By adjusting the focus adjustment button 504, the positions of the lenses 235-10, 235-14, 235-16, and 235-18 are simultaneously adjusted.

When the WFSLO image is clearly displayed, the inspector presses the WFSLO recording button 517 to store WFSLO data (WFSLO image).

[Step S4]

The inspector checks the WFSLO image displayed in the WFSLO display region 515 and stored in step S3, and determines a position for obtaining an AOSLO image. Then, the inspector guides the line of sight of the subject's eye 207 so that the position can be set, for example, on the center of the WFSLO display region 515.

There are two methods for determining the position of obtaining the AOSLO image: one is instructing a position of the fixation lamp in a fixation lamp position display region 513, and the other is clicking a desired position of the WFSLO image in the WFSLO image display region 515. A pixel in the WFSLO display region 515 and the position of the fixation lamp are associated with each other. The driving/control unit 114 automatically moves the position of the fixation lamp according to the clicked position to guide the line of sight of the subject's eye to a desired position. Since the line of sight of the subject's eye is guided by using the WFSLO image stored in step S3, it is not necessary to enter the beam emitted from the light source 201-2 to obtain the WFSLO image into the subject's eye during processing of step S4.

After confirmation that the obtaining position of the AOSLO image has moved to the center of the WFSLO display region 515, the processing proceeds to a next step. In the present exemplary embodiment, the region for obtaining the AOSLO image is a rectangular region of a predetermined size around the optical axis of the optical system illustrated in FIG. 2. In other words, the region of obtaining the AOSLO image is a rectangular region of a predetermined size around the center of the WFSLO display region 515. The region for obtaining the AOSLO image is not limited to this. The region can be arbitrarily changed.

The WFSLO image can be obtained again after the position of the fixation lamp has been changed, and it may be confirmed whether the desired position of the subject's eye 207 is at the center position of the WFSLO display region 515 to adjust the fixation position again. In this case, when entry of the measuring beam from the light source 201-3 into the subject's eye 207 is limited, the limitation is cancelled to cause the measuring beam to enter into the subject's eye 207. Thus, the desired position of the subject's eye 207 can be surely moved to the center position of the WFSLO display region 515, and applying time of the beam to the subject's eye 207 can be shortened.

[Step S44]

When the aberration measurement button 506 is selected, the driving/control unit 114 closes the shutter 291-2. When the shutter 291-2 is closed, entry of the beam emitted from the light source 201-2 into the subject's eye 207 is limited (blocked off). In response to storing the WFSLO image, the driving/control unit 114 can close the shutter 291-2. In other words, step S44 may be carried out before step S4.

[Step S45]

Then, the driving/control unit 114 opens the shutter 291-3. When the shutter 291-3 is opened, the beam emitted from the light source 201-3 enters into the subject's eye 207. For example, the fixation lamp 256 is in a lit state when the control software is activated or the execution button 501 is selected. The driving/control unit 114 causes a first measuring beam to enter into the subject's eye when the beam emitted from the fixation lamp is incident on the subject's eye. In the shutter state display region 509, the opened state of the shutter 291-3 is displayed, and the closed states of the shutters 291-1 and 291-3 are displayed.

[Steps S5 and S6]

Then, the display control unit 112 displays a Hartman image detected by the wavefront sensor 255 in a wavefront display region 514. The display control unit 112 displays aberration calculated from the Harman image in an aberration display region 511. The aberration is divided into a defocus component (µm) and all aberration amounts (µm RAM) for display. Since the positions of the focus lenses 235-10 and 235-16 of the AOSLO imaging beam and the beacon beam have been adjusted in step S3, performing aberration measurement has become possible at this step.

When the autofocus button 521 is pressed, the driving/control unit 114 automatically adjusts the positions of the lenses 235-10, 235-14, 235-16, and 235-18 to reduce a default value.

Then, when the aberration correction button 522 is pressed, the driving/control unit 114 adjusts the spatial light modulator 259 in a direction that an aberration amount becomes smaller, and the display control unit 112 displays a value of the aberration amount in real time. The driving/control unit 114 compares the aberration amount with a predetermined threshold value. When the value of the aberration amount is equal to or lower than a predetermined threshold value (0.03 µm RMS), the driving/control unit 114 automatically presses the AOSLO measurement button 507, and the processing proceeds to a next step. When the value of the aberration amount is not equal to or lower than the predetermined threshold value, the inspector may press the aberration correction temporary stop button 508 to stop the aberration correction. Then, the processing proceeds to a next step by pressing the AOSLO measurement button 507. The threshold value of the aberration amount is not limited to this threshold value. The threshold value can be arbitrarily set. When the aberration amount calculated by the aberration determination unit 113 is not equal to or lower than the predetermined threshold value for a predetermined time, the AOSLO measurement button 507 can be automatically selected by the driving/control unit 114.

[Step S66]

When the value of the aberration amount is equal to or lower than the predetermined threshold value, the driving/control unit 114 closes the shutter 291-3. In other words, when the AOSLO measurement button 507 is selected, the driving/control unit 114 closes the shutter 291-3. When the shutter 291-3 is closed, entry of the beam emitted from the light source 201-3 into the subject's eye 207 is limited (blocked off).

[Step S67]

When the shutter 291-3 is closed, the driving/control unit 114 opens the shutter 291-1. In other words, when the AOSLO measurement button 507 is selected, the driving/control unit 114 opens the shutter 291-1. When the shutter 291-1 is opened, the beam emitted from the light source 201-1 enters into the subject's eye 207. In the shutter state display region 509, the opened state of the shutter 291-1 is displayed, and the closed states of the shutters 291-2 and 291-3 are displayed.

[Step S7]

An aberration-corrected AOSLO image is displayed in the AOSLO display region 518. In the AOSLO intensity display region 519, as in the case of the WFSLO intensity display region 516, signal intensity of the AOSLO image is time-sequentially displayed.

When the signal intensity is insufficient, while watching the AOSLO intensity display region 519, the inspector adjusts a focus and a chin rest position to increase the signal intensity.

With the imaging condition setting button 523, the inspector can designate as an imaging field angle, a frame rate, and imaging time.

By adjusting the depth adjustment button 524 and moving the lens 235-10, the inspector can adjust an imaging range of the subject's eye 207 in the depth direction. Specifically, an image of a desired layer such as a photoreceptor layer, a nerve fiber layer or a pigment epithelial layer can be obtained.

When the AOSLO image is clearly displayed, the inspector presses the AOSLO recording button 520 to store AOSLO data (AOSLO image). Then, the driving/control unit 114 limits entry of the measuring beam 206-1 into the subject's eye.

[Step S77]

After the AOSLO image has been stored, the AOSLO shutter 291-1 is closed to limit entry of the measuring beam 206-1 into the subject's eye. In the shutter state display region 509, closed states of all the shutters 291-1 to 291-3 are displayed.

[Step S8]

The inspector determines whether to change the imaging position. When the imaging position is changed, the processing returns to step S4. Step S44 after the return to step S4 is omitted. On the other hand, when the imaging position is not changed, the processing proceeds to the next step. Supposing that an imaging position changing button is displayed on the liquid crystal display monitor 105, when this imaging position changing button is selected, the control PC 106 may determine that the imaging position will be changed. When the imaging position changing button is not selected for a predetermined time after the AOSLO image has been stored, the control PC 106 may determine that the imaging position will not be changed.

[Step S9]

The inspector determines whether to switch between left and right eyes. When the switching is carried out, the processing returns to step S2. On the other hand, when the left and right eyes are not switched, the processing proceeds to the next step. Supposing that a left and right eye switching button is displayed on the liquid crystal display monitor 105, when this left and right eye switching button is selected, the control PC 106 may determine that a right eye will be switched. When the left and right eye switching button is not selected for a predetermined time after the AOSLO image has been stored, the control PC 106 may determine that the right eye will not be switched.

The execution order of step S8 and step S9 may be reversed.

[Step S10]

The inspector presses the stop button 502, to stop the control software. The control software is stopped, and the series of imaging operations is ended.

<Image Confirmation>

Figure 8:
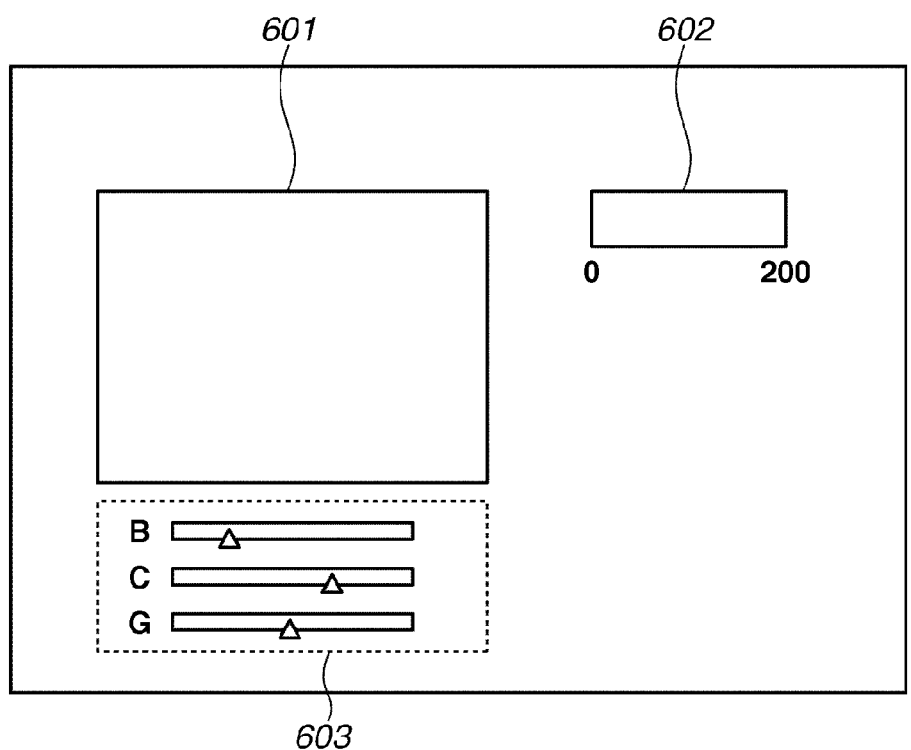
FIG. 8 illustrates an example of a configuration of an image browsing software screen of the AOSLO apparatus according to the exemplary embodiment of the present invention.

Next, referring to FIG. 8, a method for forming the data captured by the AOSLO apparatus of the present exemplary embodiment into an image for confirmation will be described. FIG. 8 illustrates an example of a configuration of an image browsing software screen according to the present exemplary embodiment.

When viewer software for making image data captured by the software control unit 110 visible is activated, the image browsing software screen illustrated in FIG. 8 is displayed in the liquid crystal monitor 105.

This viewer software can read the stored WFSLO data or AOSLO data to form an image.

The viewer software screen includes an image display region 601, an image number selection unit 602, and an image quality adjustment unit 603.

In the image display region 601, an image selected by using the image number selection unit 602, such as an AOSLO image, is displayed. A WFSLO image corresponding to the AOSLO image can be displayed in the image display region 601 by disposing a display switching unit such as a tab. Accordingly, the AOSLO image and the WFSLO image can be easily compared with each other. The AOSLO image and the WFSLO image can be displayed side by side.

The image number selection unit 602 is configured to select a desired AOSLO image from a plurality of AOSLO images obtained by the AOSLO apparatus 101. For example, the image number selection unit 602 is a slider. A position of the slider is associated with an image number of the AOSLO image. The inspector can select a desired AOSLO image by moving the slider via an instruction unit. The number of captured images varies depending on measuring time, and image numbers are added in order of time. The image number selection unit 602 is not limited to the slider. The image number selection may be performed in a region to which the image number can be directly input.

The image quality adjustment unit 603 is a slider configured to adjust image brightness, contrast, and gamma ("B", "C", and "G" in FIG. 8). Image quality can be adjusted by moving the slider left and right. The control PC 106 adjusts quality of an image such as an AOSLO image based on an input to the image quality adjustment unit 603.

The viewer software screen is not limited to the example. For example, a fixation position when the AOSLO image displayed in the image display region 601 is obtained can be displayed as a coordinate value or a drawing. Coordinates of the face rest 104 when the AOSLO image displayed in the image display region 601 is obtained may also be displayed. Further, luminance or amplitude of the AOSLO image with respect to scanning time when the AOSLO image displayed in the image display region 601 is obtained may be displayed as a graph. Information indicating a position of at least one of the lenses 235-10, 235-14, 235-16, and 235-18 when the AOSLO image displayed in the image display region 601 is obtained may be displayed.

The AOSLO image can be displayed as a moving image in the image display region 601. In this case, for parameters such as the fixation position at the time of obtaining the AOSLO image, values corresponding to the AOSLO image are sequentially displayed.

Thus, according to the present exemplary embodiment, in the case of the AOSLO apparatus, the waveforms are allocated to the light sources according to purposes by sequentially arranging, from the short wavelength side, the light source for observing the anterior eye portion, the light source for obtaining the AOSLO image, and the light source for obtaining the WFSLO image. Thus, according to the AOSLO apparatus of the present exemplary embodiment, a highly accurate AOSLO image can be obtained. In other words, a highly accurate AOSLO image can be obtained by using a wavelength relationship of the light sources suited to the AOSLO apparatus. According to the present exemplary embodiment, the wavelength determination method of each light source in the apparatus including the plurality of light sources is clarified. Further, according to the present exemplary embodiment, the wavelengths can be effectively used by setting the interval between the center wavelengths to be double or more of the sum of ½ of half-value full widths of the adjacent light sources. Conventionally, any method for determining wavelengths to effectively use the wavelengths has not been disclosed. However, as in the case of the present invention, when the interval between the center wavelengths is set double or more of the sum of ½ of half-value full widths of the adjacent light sources, unnecessary widening of the interval between the center wavelengths can be prevented, and the wavelengths can be effectively used according to sensitivity of the sensor or desired resolution.

According to the present exemplary embodiment, the AOSLO image can be obtained while preventing the beams from simultaneously entering into the subject's eye from the plurality of light sources. Thus, reduction of image quality can be prevented while securing safety.

In a state where the beam emitted from the light source 201-3 enters into the subject's eye 207, the fixation lamp 256 is lit. Thus, movement of the subject's eye 207 can be suppressed, and aberration measurement can be accurately performed.

If entry of the measuring beam emitted from the light source 201-2 into the subject's eye is limited after storage of the WFSLO image and a position for obtaining the AOSLO image is adjusted with use of the WFSLO image, more beam amount applied to the subject can be reduced. According to the present exemplary embodiment, when the limiting of the entry of the measuring beam into the subject's eye 207 is cancelled, time from turning-OFF of the light sources 201-1 to 201-3 to emission of the beam is not required. Thus, reduction of image quality can be prevented while securing safety, and inspection time can be prevented from becoming longer.

Since the beams emitted from the light sources 201-1 to 201-3 do not simultaneously enter into the subject's eye, the respective beam amounts can be increased, and an accurate AOSLO image can be obtained.

Since the opened/closed states of the shutters 291-1 to 291-3 are displayed in the shutter state display region 509, the inspector can clearly and easily know which of the measuring beams 206-1 to 206-3 is being applied to the subject's eye 207. Thus, certainty of the imaging operation is increased.

The exemplary embodiment can be applied to an anterior eye. The exemplary embodiment has been directed to the eyes. However, the present invention can be applied to other portions such as skins or internal organs.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2012-126191 filed Jun. 1, 2012, which is hereby incorporated by reference herein in its entirety.

What is claimed is:

1. An ophthalmologic apparatus comprising:
   a first light source configured to emit a first measuring light;
   a second light source configured to emit a second measuring light having a center wavelength longer than that of the first measuring light;
   a third light source configured to emit a third measuring light having a center wavelength shorter than that of the first measuring light;
   an aberration measurement unit configured to measure aberration caused by a subject's eye with use of a return light of the first measuring light from the subject's eye;
   a correction unit configured to correct aberration of a return light of the second measuring light from the subject's eye caused by the subject's eye based on the aberration measured by the aberration measurement unit;
   a first acquisition unit configured to obtain a first image of the subject's eye by using the return light of the second measuring light from the subject's eye, the aberration of which has been corrected by the correction unit; and
   a second acquisition unit configured to obtain an anterior eye portion image of the subject's eye to be used for alignment, by using a return light of the third measuring light from the subject's eye.

2. The ophthalmologic apparatus according to claim 1, wherein the center wavelength of the second measuring light is equal to or less than 1000 nm, and the center wavelength of the third measuring light is equal to or more than 700 nm.

3. The ophthalmologic apparatus according to claim 1, further comprising:
   a fourth light source configured to emit a fourth measuring light having a center wavelength longer than that of the second measuring light; and
   a third acquisition unit configured to obtain a second image of the subject's eye used for determining an obtaining position of the first image of the subject's eye by using a return light of the fourth measuring light from the subject's eye.

4. The ophthalmologic apparatus according to claim 3, wherein the center wavelength of the third measuring light is equal to or more than 700 nm, and a center wavelength of the fourth measuring light is equal to or less than 1000 nm.

5. The ophthalmologic apparatus according to claim 4, wherein:
   the first image is a fundus image of the subject's eye; and
   the second image is a fundus image of the subject's eye having a field angle wider than that of the first image.

6. The ophthalmologic apparatus according to claim 1, wherein an interval between the center wavelength of the first measuring light and the center wavelength of the second measuring light is a value based on respective half-value full widths of the first measuring light and the second measuring light.

7. The ophthalmologic apparatus according to claim 6, wherein the interval between the center wavelength of the first measuring light and the center wavelength of the second measuring light is a value based on a value n (n is a natural number) times larger than a sum of 1/n of half-value full widths of the first measuring light and the second measuring light.

8. The ophthalmologic apparatus according to claim 7, wherein the interval between the center wavelength of the first measuring light and the center wavelength of the second measuring light is a value equal to or higher than the value n times larger than the sum of 1/n of half-value full widths of the first measuring light and the second measuring light.

9. The ophthalmologic apparatus according to claim 7, wherein n=2 is set.

10. The ophthalmologic apparatus according to claim 1, further comprising:
    a third light source configured to emit a third measuring light having a center wavelength longer than that of the first measuring light; and
    a third acquisition unit configured to obtain a second image of the subject's eye used for determining an obtaining position of the first image of the subject's eye by using a return light of the third measuring light from the subject's eye.

11. The ophthalmologic apparatus according to claim 10, wherein the center wavelength of the second measuring light is equal to or more than 700 nm, and a center wavelength of the third measuring light is equal to or less than 1000 nm.

12. The ophthalmologic apparatus according to claim 10, wherein:
    the first image is a fundus image of the subject's eye; and
    the second image is a fundus image of the subject's eye having a field angle wider than that of the first image.

13. The ophthalmologic apparatus according to claim 10, wherein an interval between the center wavelength of the first measuring light and the center wavelength of the third measuring light is a value based on respective half-value full widths of the first measuring light and the third measuring light.

14. The ophthalmologic apparatus according to claim 13, wherein the interval between the center wavelength of the first measuring light and the center wavelength of the third measuring light is a value based on a value n (n is a natural number) times larger than a sum of 1/n of half-value full widths of the first measuring light and the third measuring light.

15. An ophthalmologic apparatus comprising a plurality of light sources configured to emit measuring light of different center wavelengths,
    wherein an interval between the center wavelengths adjacent to each other is a value based on respective half-value full widths of the plurality of adjacent measuring light.

16. The ophthalmologic apparatus according to claim 15, wherein the interval between the center wavelengths adjacent to each other is a value based on a value n (n is a natural number) times larger than a sum of 1/n of half-value full widths of the plurality of adjacent measuring light.

17. The ophthalmologic apparatus according to claim 16, wherein the interval between the center wavelengths adjacent to each other is a value equal to or higher than the value n times larger than the sum of 1/n of half-value full widths of the plurality of adjacent measuring light.

18. The ophthalmologic apparatus according to claim 15, wherein n=2 is set.

19. An ophthalmologic apparatus comprising:
    a first light source configured to emit a first measuring light;
    a second light source configured to emit a second measuring light having a center wavelength shorter than that of the first measuring light;
    an aberration measurement unit configured to measure aberration caused by a subject's eye;
    a correction unit configured to correct aberration of a return light of the first measuring light from the subject's eye caused by the subject's eye based on the aberration measured by the aberration measurement unit;
    a first acquisition unit configured to obtain a first image of the subject's eye by using the return light of the first measuring light from the subject's eye, the aberration of which has been corrected by the correction unit; and a second acquisition unit configured to obtain an anterior eye portion image of the subject's eye to be used for alignment, by using a return light of the second measuring light from the subject's eye.

20. The ophthalmologic apparatus according to claim 19, wherein the center wavelength of the first measuring light is equal to or less than 1000 nm, and the center wavelength of the second measuring light is equal to or more than 700 nm.

* * * * *